(12) United States Patent
Linares et al.

(10) Patent No.: US 6,782,751 B2
(45) Date of Patent: Aug. 31, 2004

(54) PIPE INSPECTION SYSTEMS AND METHODS

(75) Inventors: Lionel S. Linares, Spring, TX (US); Kenneth R. Newman, Willis, TX (US)

(73) Assignee: CTES, L.C., Conroe, TX (US)

( * ) Notice: Subject to any disclaimer, the term of this patent is extended or adjusted under 35 U.S.C. 154(b) by 0 days.

(21) Appl. No.: 10/243,996

(22) Filed: Sep. 13, 2002

(65) Prior Publication Data

US 2004/0050167 A1 Mar. 18, 2004

(51) Int. Cl.[7] ............................................... G01N 29/28
(52) U.S. Cl. ....................................... 73/622; 73/644
(58) Field of Search ........................... 73/620, 622, 623, 73/644

(56) References Cited

U.S. PATENT DOCUMENTS

| | | | | |
|---|---|---|---|---|
| 3,986,389 A | | 10/1976 | Mesina et al. ............... 73/67.9 |
| 4,010,635 A | | 3/1977 | Patsey ......................... 73/67.8 |
| 4,019,373 A | * | 4/1977 | Freeman et al. .............. 73/644 |
| 4,213,345 A | * | 7/1980 | Dufour ......................... 73/637 |
| 4,279,167 A | * | 7/1981 | Erb et al. .................. 73/861.25 |
| 4,404,853 A | | 9/1983 | Livingston ..................... 73/622 |
| 4,475,399 A | | 10/1984 | Livingston ..................... 73/622 |
| 4,487,072 A | | 12/1984 | Livingston ..................... 73/622 |
| 4,541,064 A | | 9/1985 | Livingston ................... 364/552 |
| 4,569,229 A | | 2/1986 | de Halleux ................... 73/597 |
| 4,718,277 A | * | 1/1988 | Glascock ...................... 73/622 |
| 4,870,866 A | | 10/1989 | Slack ........................... 73/599 |
| 5,078,149 A | * | 1/1992 | Katsumata et al. ........... 600/459 |
| 5,280,722 A | * | 1/1994 | Madaras ....................... 73/588 |
| 5,313,837 A | | 5/1994 | Haynes ......................... 73/622 |
| 5,460,046 A | | 10/1995 | Maltby et al. ................. 73/623 |
| 5,585,565 A | * | 12/1996 | Glascock et al. ............. 73/644 |
| 5,600,069 A | | 2/1997 | Girndt et al. .................. 73/622 |
| 5,656,786 A | | 8/1997 | Curtis, Jr. et al. .......... 73/865.8 |
| 5,867,275 A | | 2/1999 | Curtis, Jr. et al. ........... 356/384 |
| 5,914,596 A | | 6/1999 | Weinbaum .................... 324/228 |
| 6,678,403 B1 | * | 1/2004 | Wilk ........................... 382/152 |

FOREIGN PATENT DOCUMENTS

| | | |
|---|---|---|
| GB | 2 124 379 A | 2/1984 |
| GB | 2 280 507 A | 2/1995 |

OTHER PUBLICATIONS

Truweld (tm) Ultrasonic Weld Line Inspection System, Tuboscope, 2001.

* cited by examiner

*Primary Examiner*—Hezron Williams
*Assistant Examiner*—Rose M. Miller
(74) *Attorney, Agent, or Firm*—Guy McClung

(57) ABSTRACT

Systems and methods for ultrasonically inspecting pipe, the pipe having a longitudinal axis, the methods in certain aspects including compressing with a compressing force an elastomeric element between an ultrasonic probe of an ultrasonic pipe inspection system and a pipe to be inspected; and, in certain aspects, the systems and methods including placing a coupling between the elastomeric element and the pipe, wherein the elastomeric element surrounds the pipe; and, in certain aspects, a system for ultrasonically inspecting pipe, the system with a housing, a packer element in the housing with an opening through which a pipe to be inspected is passable, and at least one ultrasonic probe in or on the housing useful in conjunction with an ultrasonic apparatus for inspecting pipe.

23 Claims, 4 Drawing Sheets

PIPE INSPECTION SYSTEMS AND METHODS

BACKGROUND OF THE INVENTION

1. Field of the Invention

The present invention is directed to ultrasonic pipe inspection systems and methods.

2. Description of Related Art

Many systems have been developed to inspect pipe. A variety of these systems measure the diameter, ovality, and wall thickness. They also look for flaws in the pipe such as cracks and pits. Some versions of these systems have been adapted for inspecting coiled tubing (CT). These systems can be categorized in three major types: nuclear—some type of radiation such as gamma rays are passed through the pipe and the reflections are measured; electromagnetic—magnetic flux is passed through the pipe and the flux flow or flux leakage is measured; and ultrasonic (UT)—ultrasonic sound is passed through the pipe and the reflections are measured. Nuclear measurements require a nuclear source, which makes them impractical for many applications.

Systems using electromagnetic measurements have been used for diameter and ovality measurement, and for finding anomalies, flaws and defects in the pipe, such as cracks, but often such systems have not proven accurate for measuring the wall thickness in one localized area of the pipe. As and example, an electromagnetic inspection system for CT is discussed in U.S. Pat. No. 5,914,596. UT inspection systems have been used for measuring the localized wall thickness of a tubular. They are also capable of An exemplary UT system for inspecting CT is shown in U.S. Pat. No. 5,303,592.

Wall thickness measurement is often important when inspecting CT. Some services, such as CT fracturing, tend to erode the inner surface of the CT in some areas. Also, the CT wall may be worn when used in wells with chrome tubulars. Thus, UT inspection is desirable as a method of locating CT dimensional variations, flaws, defects, and/or anomalies.

With UT inspection systems an ultrasonic probe or probes are acoustically "coupled" with the pipe. A UT probe contains both the UT transmitter and the UT receiver, which may or may not be the same device. Alternatively one probe may contain the transmitter and a different probe may contain the receiver. "Probe" refers to all types of UT devices used to make UT measurements and can include, but is not limited to, systems that use a spacer in front of a probe, the spacer sometimes referred to as a "delay line" which modifies the acoustic response of the system and protects the probe. The probe is in contact with a coupling medium which is in contact with the pipe. The UT sound waves pass from the probe, through the coupling medium and into the pipe. Often a liquid, such as water, is used as a coupling medium, as in U.S. Pat. No. 5,303,592. A circulating system is often used to circulate the coupling fluid and keep it clean. Seals are used to prevent the coupling fluid from escaping around the pipe. Often the coupling fluid treatment and sealing system makes UT systems such as the one described in U.S. Pat. No. 5,303,592 difficult to use in some applications.

In one prior art effort to avoid problems with coupling fluid systems, a UT probe is inserted inside of a wheel which rolls along the pipe. An example of such a system is shown in U.S. Pat. No. 4,202,216. The UT probe presses against the inside surface of a tire. The outside surface of the tire is pressed against the pipe. Alternatively the inside of the tire is filled with a coupling fluid which serves as a coupling medium between the probe and the inside surface of the tire. These wheel-probe based UT systems may be too complex for some pipe inspection applications. Alternatively the probes and coupling fluid may be in a cushion or pad which is placed against the pipe. Usually an additional coupling fluid must be sprayed on the pipe to provide good coupling between the pad and the pipe. These wheel probes use a solid tire made of a material through which the sound waves will pass, such as polyurethane or a rubber compound.

Many efforts have been made to mark CT in some way so that reference points along a CT string can be easily located. Magnetic markings, paint markings, and surface etching are some of the attempted methods. Such reference points are used to verify a depth or length measurement or to determine a location along a string.

There is a need for a UT pipe inspection system which does not require a complicated coupling fluid system and can be used easily in oilfield service, pipeline and pipe manufacturing environments. There is a need for an accurate and efficient method for providing easily sensed or recognized markings on a tubular member used in wellbore operations.

SUMMARY OF THE PRESENT INVENTION

In certain embodiments, the present invention discloses methods for ultrasonically inspecting pipe, the pipe having a longitudinal axis, the method including compressing an elastomeric element with a compressing force from a piston or other compressing member, the elastomeric element between an ultrasonic probe (or probes) of an ultrasonic pipe inspection system and a pipe to be inspected, the compressing force forcing the elastomeric element generally radially against the pipe and/or forcing the elastomeric element against the probe(s), and the compressing force in the general direction of the longitudinal axis of the pipe, at an angle to the pipe, or, on one particular aspect, normal thereto. In other aspects the compressing member and its associated structures and mechanisms are deleted, but a packer element is used as the elastomeric member which is positioned in a housing with one or more ultrasonic probes within the housing, within the elastomeric member, or affixed to and outside of the housing.

The present invention, in certain embodiments, discloses a method for performing UT pipe inspection using a packer element as the primary coupling medium between the UT probe and the pipe. A packer element is typically used to seal around a pipe, separating the fluids in a well from the atmosphere. In certain aspects when the tubular string is CT, a stripper packer is used. U.S. Pat. No. 5,566,753 shows two types of CT stripper packers which are common. In the case of drilling with jointed pipe a stripper packer (U.S. Pat. No. 4,486,025) and/or an annular BOP and/or rotating BOP contains the packer element(s). In the case of hydraulic work-over (often known as "snubbing") operations, several types of sealing mechanisms containing packer elements may be used, including stripper bowls and annular BOPS, as are discussed in U.S. Pat. No. 5,988,274. Stripper packer apparatuses useful with systems according to the present invention include, but ar not limited to, those with pistons or rams that apply force either generally radially (at a right angle to the pipe) or generally in the direction of the longitudinal axis of the pipe.

In certain aspects the elastomeric or packing elements in systems and methods according to the present invention are made of an elastomeric material such as, but not limited to, a rubber compound, polypropylene, polytetrafluoroethylene, polyvinylchloride, plastisols, and viton (tm) material. The elements may be composed of a single piece made of one or more elastomeric material(s), or may be composed of multiple pieces made of one or more elastomeric materials. Many methods can be used to compress the packing element against the pipe to form a pressure seal. Techniques according to the present invention for inspecting pipe through an elastomeric element may be used in any of the aforementioned devices. These techniques may also, according to the present invention, be used in a device with an elastomeric element and compression apparatus built for performing pipe inspection which may or may not also serve as a pressure barrier.

In certain aspects according to this invention, an element is compressed between UT probe(s) and the wall of the pipe, to form the primary coupling media. A thin film of a fluid may or may not be placed between the probe(s) and the element, and/or between the element and the pipe to enhance the acoustic coupling. The probe(s) are then used to inspect the pipe using known UT inspection techniques and signal generation and processing systems.

In certain aspects, to enhance the elastomeric material's ability to transmit acoustic waves, multiple elastomeric materials are used. For example, and not by way of limitation, the material between the UT probe(s) and the pipe may be selected for its ability to transmit acoustic waves, while the remaining material may be selected for its ability to form a pressure seal. The UT probe(s) or a portion of them may be embedded in the element, affixed to it, or screwed into it. In certain embodiments, the acoustic material does not go all the way through the elastomeric element and does not contact the pipe to prevent wearing of the acoustic material by contact with the pipe; e.g., in one particular embodiment there is about one half inch of elastomeric material between the acoustic material and the pipe.

In certain embodiments systems according to the present invention to use one or a plurality of areas or rings of increased or decreased wall thickness on pipe, tubulars or coiled tubing. It is within the scope of this invention to position one or more of such areas at known locations so that, upon sensing of the presence of the area(s), the amount of pipe, etc. and/or the location of an item thereon can be accurately calculated and/or displayed. For example, positioning an area of increased wall thickness with a known wall thickness that acts as a sensible signature for that area a thousand feet above the end of coiled tubing makes it possible for an operator to know when a thousand feet of the coiled tubing has been inserted into a wellbore and, in retrieving the coiled tubing from the wellbore, to know when there is still a thousand feet left in the wellbore to be retrieved. Positioning an area of known increased or decreased wall thickness at a known distance from an apparatus or device on a tubular string permits accurate locating of the device within the wellbore and/or provides an accurate indication of the location. Similarly, the depth of a wellbore and/or the depth at which is located the the end of tubular string can be determined by using one or more areas of known sensible and/or unique wall thickness at known locations on a tubular string. In one aspect, a sensible area of known and/or unique wall thickness near the end of coiled tubing provides an indication to an operator that the end of the tubing is near as it is being withdrawn from a wellbore so that appropriate action can be taken, e.g., slowing down of the rate of tubing retrieval to prevent damage to equipment. In other embodiments as series is used on a pipe, etc., of spaced-apart areas or rings of a wall thickness that differs from the areas on either side of the series and such areas or rings can be of the same or of different wall thicknesses themselves. In one aspect simply the number of areas or rings of different wall thickness is used to provide a locating structure.

The present invention recognizes and addresses the previously mentioned problems and long-felt needs and provides a solution to those problems and a satisfactory meeting of those needs in its various possible embodiments and equivalents thereof. To one skilled in this art who has the benefits of this invention's realizations, teachings, disclosures, and suggestions, other purposes and advantages will be appreciated from the following description of preferred embodiments, given for the purpose of disclosure, when taken in conjunction with the accompanying drawings. The detail in these descriptions is not intended to thwart this patent's object to claim this invention no matter how others may later disguise it by variations in form or additions of further improvements.

DESCRIPTION OF THE DRAWINGS

A more particular description of embodiments of the invention briefly summarized above may be had by references to the embodiments that are shown in the drawings which form a part of this specification. These drawings illustrate certain preferred embodiments and are not to be used to improperly limit the scope of the invention that may have other equally effective or legally equivalent embodiments.

DESCRIPTION OF EMBODIMENTS PREFERRED AT THE TIME OF FILING FOR THIS PATENT

Figure 1:
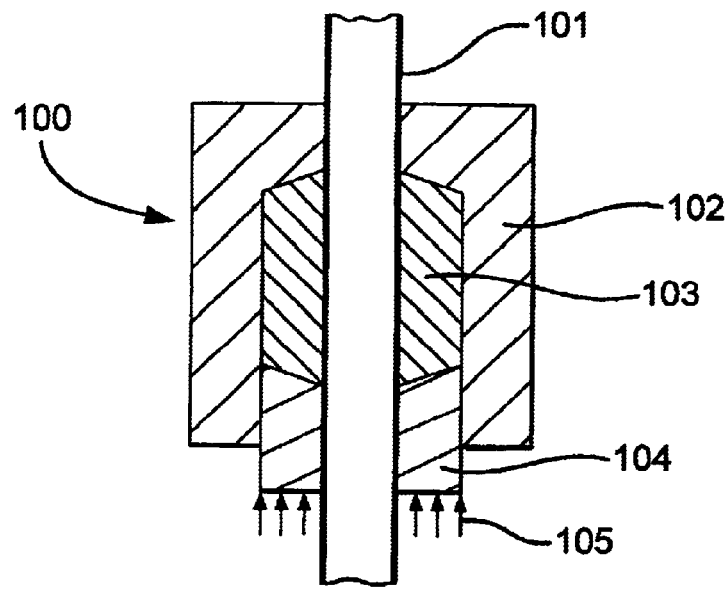
FIG. 1 is a side cross-section view of a prior art stripper packer apparatus.

FIG. 1 shows a prior art stripper packer system 100. Pipe 101 (which may be any tubular or CT), passes through the stripper packer. The stripper packer has an outer housing 102, a packer element 103, and a movable piston 104. Pressure or force 105 is applied to the piston, causing it to compress the packer element against the pipe 101.

Figure 2:
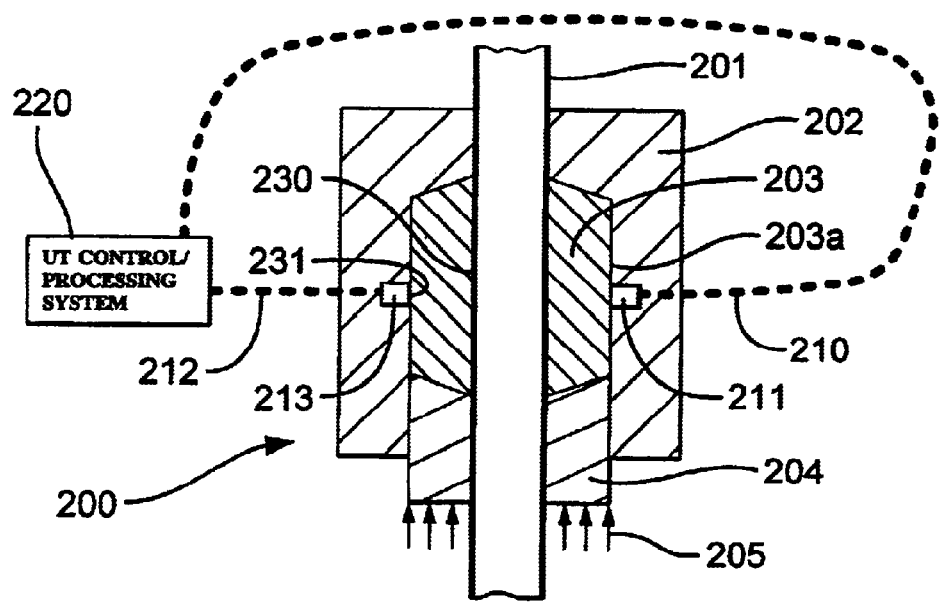
FIGS. 2–5, 6B and 7 are side cross-section views of systems according to the present invention.
Figure 3:
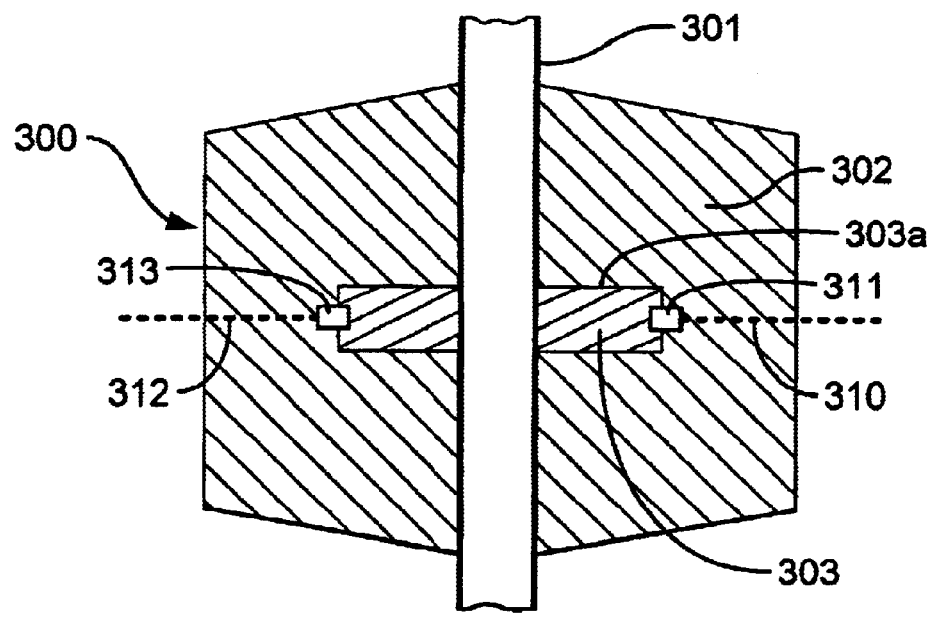

FIG. 2 shows a system 200 according to the present invention with UT pipe inspection capabilities. A generally cylindrical hollow pipe 201 passes through a housing 202 with an elastomeric element 203 in a cavity 203a. The element 203 surrounds the pipe and is compressed by force or pressure 205 on a piston 204. UT probes 211 and 213 are affixed to or embedded in a housing 202. Electrical wires 210 and 212 from the probes 211 and 213, respectively, pass out of the housing 202 and to a UT control/processing system 220 (which may also display results). When the element 203 is subjected to a compressing force or pressure 205 (in a direction generally in the direction of a longitudinal axis of the pipe 201), the element 203 is compressed, including in a generally radial direction against both the UT probes 211 and 213 and against the pipe 201. This compressive loading enhances the acoustic coupling required for the sound wave to pass from the probe to the pipe. The sonic coupling may be improved if the pipe is coated with a fluid, e.g. but not limited to oil. Also, the coupling may be improved if a fluid such as grease is applied between the probes 211, 213 and the element 203, i.e., grease indicated at 231; and also applied between the element 203 and the pipe 201, i.e., grease indicated at 203. An end portion of each of the UT probes may extend slightly into the cavity 203a to insure good contact of the probes with the element 203 (e.g., as shown in FIG. 3). The elastomeric element 203 may be a stripper packer.

FIG. 3 shows an elastomeric element 302 according to the present invention useful with any system according to the present invention, which contains UT probes 311 and 313 in the elastomeric element 302. In certain aspects the elastomeric element 302 is a packing element of a stripper packer system. The probes 311, 313 are connected to and in communication with a UT inspection system (not shown; like the system 220, FIG. 2) by wires 310 and 312, respectively. The elastomeric element 302 may contain multiple regions or parts including a part 303. In one aspect the elastomer in the elastomeric element 302 is chosen for its sealing capabilities, and the material in the region or part 303 is chosen for its acoustic transmission capabilities. The part 303 may, according to the present invention, be a bladder or fluid bag. The probes inner ends extend slightly into a cavity 303a that contains the elastomeric element 303.

Figure 4:
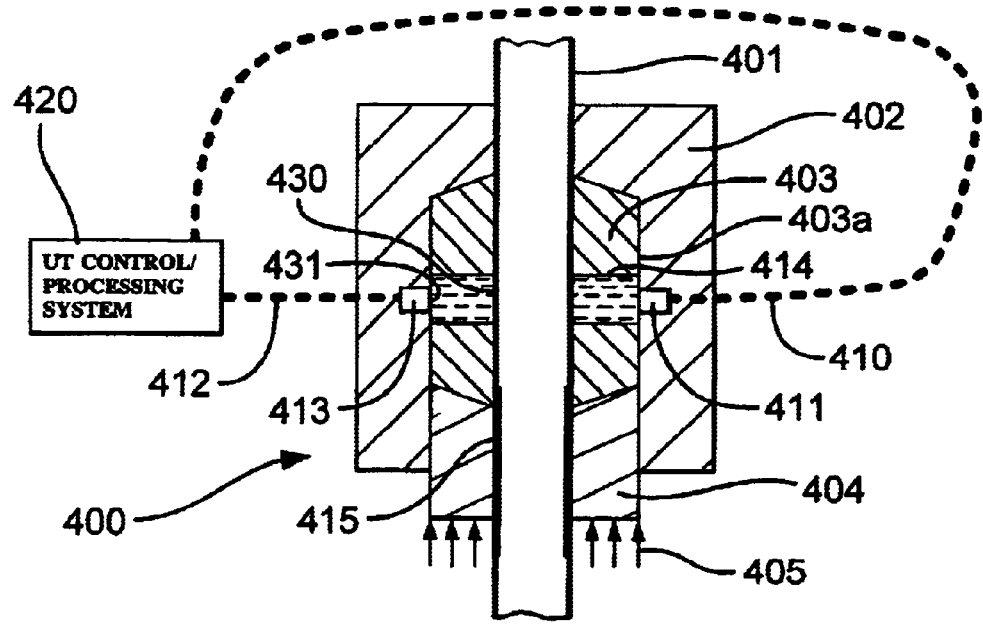

FIG. 4 shows a system 400 according to the present invention with UT pipe inspection capabilities. A generally cylindrical hollow pipe 401 passes through a housing 402 with an elastomeric element 403 in a cavity 403a. The element 403 has an intermediate portion 414 which, in one aspect, is made of material that enhances acoustic transmission. The element 403 and its intermediate portion 414 surround the pipe and are compressed by force or pressure 405 on a piston 404. UT probes 411 and 413 are affixed to or embedded in a housing 402. Electrical wires 410 and 412 from the probes 411 and 413, respectively, pass out of the housing 402 and to a UT control/processing system 420 (like the system 220, FIG. 2). When the element 403 is subjected to a compressing force or pressure 405 (in a direction generally in the direction of a longitudinal axis of the pipe 401), the element 403 and the intermediate portion 414 are compressed, including in a generally radial direction against both the UT probes 411 and 413 and against the pipe 401. This compressive loading enhances the acoustic coupling required for the sound wave to pass from the probe to the pipe. The sonic coupling may be improved if the pipe is coated with a fluid, e.g. but not limited to oil. Also, the acoustic coupling may be improved if a fluid such as grease is applied between the probes 411, 413 and the element 403, i.e., grease indicated at 431; and also applied between the element 403 and the pipe 401, i.e., grease indicated at 430. An end portion of each of the UT probes may extend slightly into the cavity in which the element 403 is positioned to insure good contact of the probes with the packer element. The wall thickness of the pipe 401 varies with a thicker part 415 as compared to other parts of the pipe. Any tubular, pipe or CT herein may have one or more areas of rings of differing wall thickness.

Figure 5:
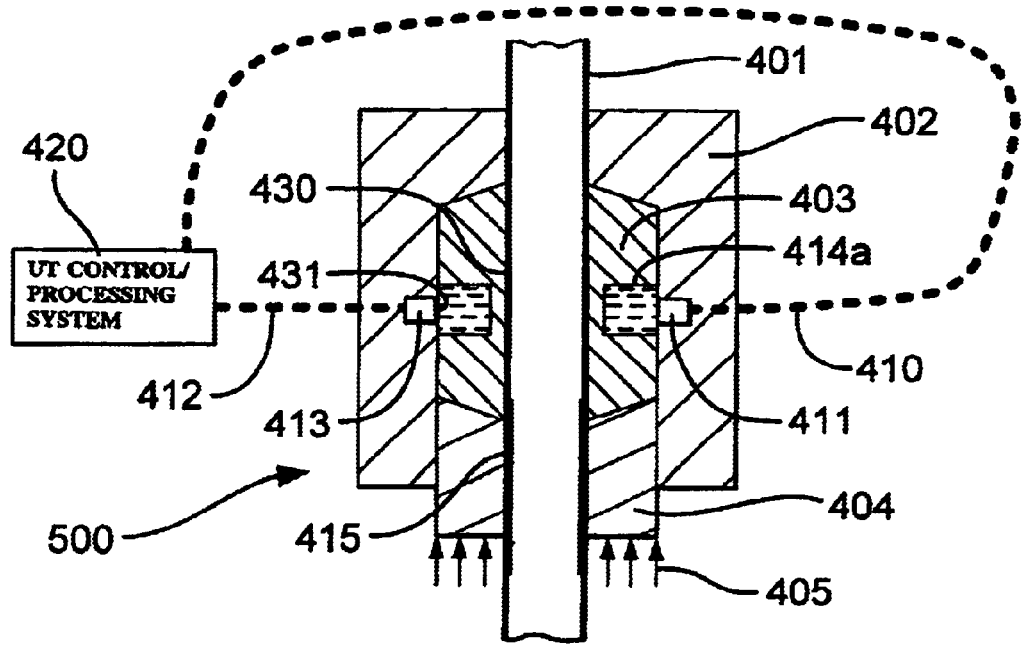

FIG. 5 shows an alternative embodiment of the system 400 of FIG. 4, and like numerals indicate like parts. Intermediate portion 414a (like the intermediate portion 414, FIG. 4) does not contact the pipe 401 and may, in certain aspects, be made of material that enhances acoustic transmission. A portion of an element 403a (like the element 403, FIG. 4) is between the pipe 401 and the intermediate portion 414a.

Figure 6A:
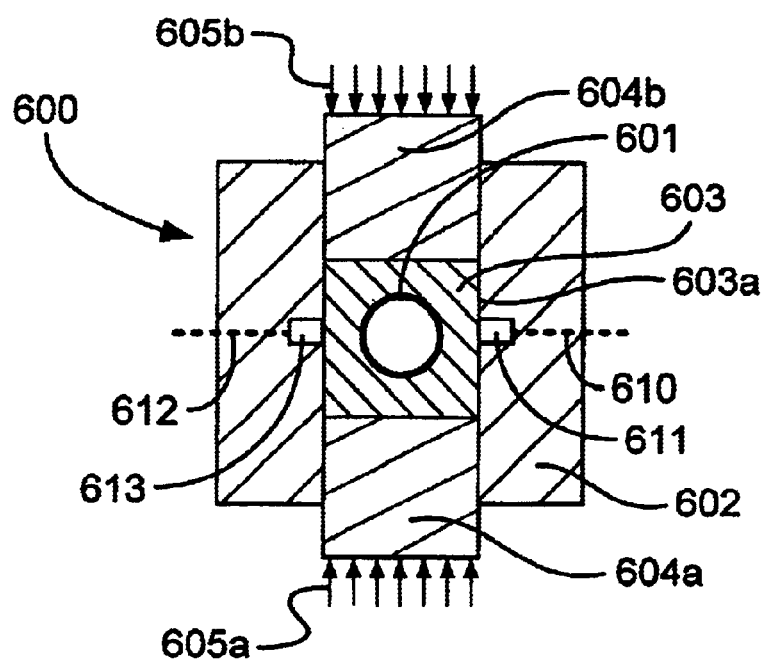
FIG. 6A is a top view of the system of FIG. 6B.
Figure 6B:
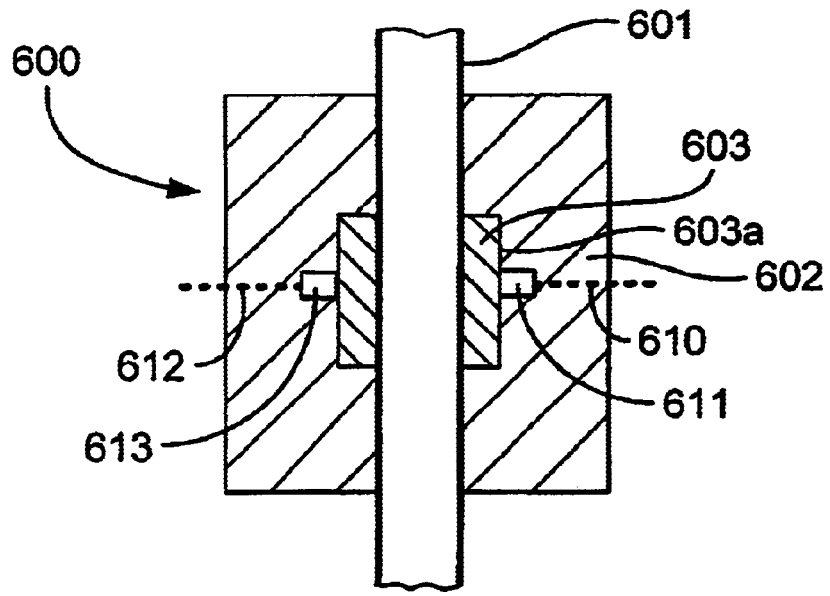

FIGS. 6A and 6B show a system 600 according to the present invention which has a system with radially movable rams 604a, 604b movable in a housing 602. Forces 605a, 605b on the rams 604a, 604b, respectively, move the rams. The rams apply a radial (normal to the longitudinal axis of pipe 601) force to an elastomeric element 603 in a housing cavity 603a. UT probes 611, 613 are each positioned within part of the housing 602 (but it is within the scope of this invention to position the probes in the packing element or to position them as are positioned any other probe disclosed herein and it is within the scope of this invention to use radially moving compressing members in any of the embodiments disclosed herein). The housing 602 is made of a plurality of assemblable and disassemblable parts. The UT probes 611, 613 are connected to a processing system (not shown, like the system 220, FIG. 2) by wires 610, 612, respectively.

It is within the scope of this invention to use one or a plurality of areas of increased or decreased wall thickness on pipe, tubulars or coiled tubing for use in wellbore operations, and to position one or more of such areas at known locations so that, upon sensing of the presence of the area(s), the amount of pipe, etc. and/or the location of an item thereon can be accurately calculated and/or displayed. For example, positioning an area of increased wall thickness with a known wall thickness that acts as a sensible signature for that area a thousand feet above the end of coiled tubing makes it possible for an operator to know when a thousand feet of the coiled tubing has been inserted into a wellbore and, in retrieving the coiled tubing from the wellbore, to know when there is still a thousand feet left in the wellbore to be retrieved. Positioning an area of known increased or decreased wall thickness at a known distance from an apparatus or device on a tubular string permits accurate locating of the device within the wellbore and/or provides an accurate indication of the location. Similarly, the depth of a wellbore and/or of the end of string can be determined by using one or more areas of known sensible wall thickness at known locations on a tubular string. In one aspect, a sensible area of known and/or unique wall thickness near the end of coiled tubing provides an indication to an operator that the end of the tubing is near as it is being withdrawn from a wellbore so that appropriate action can be taken, e.g., slowing down of the rate of tubing retrieval to prevent damage to equipment. Naturally occurring areas or rings of different wall thickness can, within the scope of the present invention, be used as the areas or rings described above.

Figure 7:
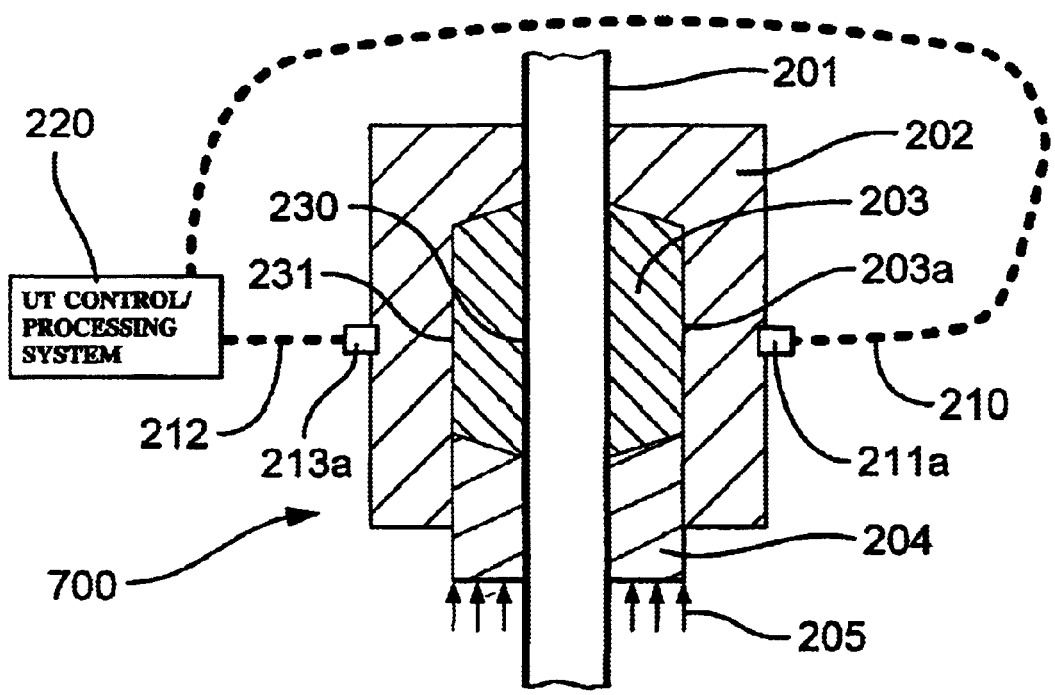

FIG. 7 illustrates a system 700 which is an alternative embodiment of the system 200, FIG. 2, and like numerals indicate like parts. UT probes 211a and 213a (like the UT probes 211 and 213, FIG. 2) are connected to the exterior of the housing 202. As shown, ends of the probes 211 and 213 project slightly into the housing 202; but it is within the scope of the present invention for the UT probes to be completely outside of or embedded in the housing 202. In certain aspects the housing 202 is made of material suitable for acoustic transmission. In certain aspects a metal housing, e.g., but not limited to, one made of steel, acts as a delay line.

The present invention, therefore, in a least certain embodiments, provides a method for ultrasonically inspecting pipe, the pipe having a longitudinal axis, the method including compressing with a compressing force an elastomeric element between an ultrasonic probe apparatus of an ultrasonic pipe inspection system and a pipe to be inspected thereby forcing the elastomeric element against the pipe.

The present invention, therefore, in a least certain embodiments, provides a system for ultrasonically inspecting pipe, the pipe having a longitudinal axis, the system including at least one ultrasonic apparatus for transmitting ultrasonic sound waves to a pipe to be inspected, for receiving reflected waves back from the pipe, and for producing signals indicative of a parameter of the pipe (e.g., but not limited to, ovality using two probes orthogonal to each other; and wall thickness and diameter suing two opposed probes) the at least one ultrasonic apparatus having at least one ultrasonic probe, control apparatus for controlling the at least one ultrasonic apparatus, processing apparatus for processing signals from the at least one ultrasonic apparatus, an elastomeric element for contacting the pipe and for contacting the at least one ultrasonic probe, the at least one ultrasonic probe located in or adjacent the elastomeric element, and apparatus for applying compressive force to the elastomeric element.

The present invention, therefore, in a least certain embodiments, provides a system for ultrasonically inspecting pipe, the pipe having a longitudinal axis, the system including at least one ultrasonic apparatus for transmitting ultrasonic sound waves to a pipe to be inspected, for receiving reflected waves back from said pipe, and for producing signals indicative of a parameter of said pipe, the at least one ultrasonic apparatus having at least one ultrasonic probe, control apparatus for controlling the at least one ultrasonic apparatus, processing apparatus for processing signals from the at least one ultrasonic apparatus, an elastomeric element for contacting the pipe and for contacting the at least one ultrasonic probe, the at least one ultrasonic probe located in or adjacent the elastomeric element, apparatus for applying compressive force to the elastomeric element, wherein the elastomeric element is a stripper element of a stripper packer system, wherein the stripper packer system is from the group consisting of a coiled tubing stripper packer system, a drilling stripper packer system, and a hydraulic workover stripper packer system, and wherein the at least one ultrasonic probe is mounted in, embedded in, or on a housing, the elastomeric element within the housing.

The present invention, therefore, in a least certain embodiments, provides a system for ultrasonically inspecting pipe, the system including a housing, a packer element or an elastomeric element in the housing, the packer element having an opening through which a pipe to be inspected is passable, at least one ultrasonic probe within, embedded in, or on the housing, the at least one ultrasonic probe useful in conjunction with an ultrasonic apparatus for inspecting pipe.

The present invention, therefore, in a least certain embodiments, provides a method for indicating a location in a wellbore extending from an earth surface down into the earth, the method including introducing a tubular string into a wellbore, the tubular string having a substantially uniform first wall thickness along its length and at least one second area of a second wall thickness, the first wall thickness different from the second wall thickness, the second wall thickness of the at least one second area sensible by wall thickness sensing equipment, the tubular string having a string location thereon a distance from the at least one second area, sensing with the wall thickness sensing equipment the presence of the second wall thickness thereby indicating the presence of the at least one second area, sending a signal from the wall thickness sensing equipment to processing equipment, and determining with the processing equipment the position of the string location within the wellbore All patents referred to herein by number are incorporated fully herein for all purposes. The present invention as disclosed herein is well adapted to carry out the objectives set forth. Certain changes can be made in the subject matter without departing from the spirit of this invention. It is realized that changes are possible within the scope of this invention and it is intended that each element or step recited in any of the following claims be understood as referring to all equivalent elements or steps. The following claims are intended to cover the invention as broadly as legally possible in whatever form it may be utilized. This specification and the claims that follow are in accordance with all of the requirements of 35 U.S.C. § 112. The inventors may rely on the Doctrine of Equivalents to determine and assess the scope of their invention and of the claims that follow as they may pertain to apparatus not materially departing from, but outside of, the literal scope of the invention as set forth in the following claims.

What is claimed is:

1. A method for ultrasonically inspecting pipe, the pipe having a longitudinal axis, the method comprising compressing with a compressing force an elastomeric element between an ultrasonic probe apparatus of an ultrasonic pipe inspection system and a pipe to be inspected thereby forcing the elastomeric element against the pipe, wherein the compressing force is applied generally in the direction of the longitudinal axis of the pipe.

2. The method of claim 1 further comprising placing a coupling fluid between the elastomeric element and the pipe.

3. The method of claim 2 wherein the coupling fluid is from the group consisting of water, oil and grease.

4. The method of claim 1 wherein the elastomeric element surrounds the pipe.

5. The method of claim 1 wherein the elastomeric element is a packing element.

6. The method of claim 5 wherein the packing element is a stripper packer.

7. The method of claim 6 wherein the compressing force is applied by at least one compressing member.

8. The method of claim 6 wherein the packing element is from the group consisting of a coiled tubing stripper packer, a drilling stripper packer, and a hydraulic workover stripper packer.

9. The method of claim 1 wherein the ultrasonic probe apparatus is mounted in a housing, the elastomeric element within the housing.

10. The method of claim 1 wherein the ultrasonic probe apparatus is mounted on or embedded in a housing, the elastomeric element within the housing.

11. The method of claim 1 wherein the elastomeric element is in contact with the ultrasonic probe apparatus.

12. The method of claim 1 wherein the ultrasonic probe apparatus is mounted within the elastomeric element.

13. The method of claim 1 wherein the elastomeric element comprises a first portion made of sealing material for sealing against the pipe and a second portion made of acoustic transmission material disposed between the ultrasonic probe apparatus and the pipe.

14. A method for ultrasonically inspecting pipe, the pipe having a longitudinal axis, the method comprising compressing with a compressing force an elastomeric element between an ultrasonic probe apparatus of an ultrasonic pipe inspection system and a pipe to be inspected thereby forcing the elastomeric element against the pipe, and wherein the elastomeric element is a packing element.

15. A system for ultrasonically inspecting pipe, the pipe having a longitudinal axis, the system comprising at least one ultrasonic apparatus for transmitting ultrasonic sound waves to a pipe to be inspected, for receiving reflected waves back from said pipe, and for producing signals indicative of a parameter of said pipe, the at least one ultrasonic apparatus having at least one ultrasonic probe, control apparatus for controlling the at least one ultrasonic apparatus, processing apparatus for processing signals from the at least one ultrasonic apparatus, an elastomeric element for contacting the pipe and for contacting the at least one ultrasonic probe, the at least one ultrasonic probe located in or adjacent the elastomeric element, and apparatus for applying compressive force to the elastomeric element, and wherein the elastomeric element is a stripper element of a stripper packer system.

16. The system of claim 15 wherein the stripper packer system is from the group consisting of a coiled tubing stripper packer system, a drilling stripper packer system, and a hydraulic workover stripper packer system.

17. The system of claim 15 wherein the at least one ultrasonic probe is mounted in a housing.

18. The system of claim 15 wherein the at least one ultrasonic probe contacts the elastomeric element.

19. The system of claim 15 wherein the at least one ultrasonic probe is mounted within the elastomeric element.

20. The system of claim 15 wherein the compressing force is applied generally in a direction parallel to the longitudinal axis of the pipe.

21. The system of claim 15 wherein the compressing force effects radial compression of the elastomeric element.

22. The system of claim 15 wherein the compressing force is applied by at least one compressing member.

23. A system for ultrasonically inspecting pipe, the pipe having a longitudinal axis, the system comprising at least one ultrasonic apparatus for transmitting ultrasonic sound waves to a pipe to be inspected, for receiving reflected waves back from said pipe, and for producing signals indicative of a parameter of said pipe, the at least one ultrasonic apparatus having at least one ultrasonic probe, control apparatus for controlling the at least one ultrasonic apparatus, processing apparatus for processing signals from the at least one ultrasonic apparatus, an elastomeric element for contacting the pipe and for contacting the at least one ultrasonic probe, the at least one ultrasonic probe located in or adjacent the elastomeric element, apparatus for applying compressive force to the elastomeric element, wherein the elastomeric element is a stripper element of a stripper packer system, wherein the stripper packer system is from the group consisting of a coiled tubing stripper packer system, a drilling stripper packer system, and a hydraulic workover stripper packer system, and wherein the at least one ultrasonic probe is mounted in or on a housing, the elastomeric element within the housing.

* * * * *